(12) United States Patent
Bousamra et al.

(10) Patent No.: US 8,601,005 B2
(45) Date of Patent: Dec. 3, 2013

(54) LOCATION ENABLED FOOD DATABASE

(75) Inventors: Steven A. Bousamra, Carmel, IN (US); David L. Duke, Fishers, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 307 days.

(21) Appl. No.: 13/117,783

(22) Filed: May 27, 2011

(65) Prior Publication Data
US 2012/0303638 A1    Nov. 29, 2012

(51) Int. Cl.
*G06F 17/30* (2006.01)
*A61B 5/145* (2006.01)

(52) U.S. Cl.
USPC .............. 707/752; 707/805; 600/365

(58) Field of Classification Search
USPC ............ 707/736, 751, 752, 805; 600/365
See application file for complete search history.

(56) References Cited

U.S. PATENT DOCUMENTS

| | | | |
|---|---|---|---|
| 6,269,314 B1 * | 7/2001 | Iitawaki et al. | 702/23 |
| 6,513,532 B2 | 2/2003 | Mault et al. | |
| 6,872,077 B2 | 3/2005 | Yeager | |
| 7,179,226 B2 | 2/2007 | Crothall et al. | |
| 7,396,330 B2 | 7/2008 | Banet et al. | |
| 7,525,450 B2 | 4/2009 | Miller et al. | |
| 7,789,828 B2 | 9/2010 | Clapp | |
| 7,805,515 B2 | 9/2010 | Riley | |
| 2002/0109600 A1 | 8/2002 | Mault et al. | |
| 2003/0040821 A1 * | 2/2003 | Case | 700/90 |
| 2003/0208409 A1 | 11/2003 | Mault | |
| 2005/0010087 A1 | 1/2005 | Banet et al. | |
| 2005/0075903 A1 | 4/2005 | Piccionelli et al. | |
| 2005/0113650 A1 | 5/2005 | Pacione et al. | |
| 2005/0250458 A1 | 11/2005 | Graham et al. | |
| 2008/0058615 A1 | 3/2008 | Clapp et al. | |
| 2008/0076971 A1 | 3/2008 | Clapp | |

(Continued)

FOREIGN PATENT DOCUMENTS

WO    WO 02/05702 A2    1/2002

OTHER PUBLICATIONS

A. Forsyth, L. Lytle, and D. Van Riper, "Finding food: Issues and challenges in using Geographic Information Systems to measure food access", National Institute of Health (www.ncbi.nlm.nih.gov), Journal of transport and land use, 2010, pp. 1-16.*

(Continued)

*Primary Examiner* — Cheryl Lewis
(74) *Attorney, Agent, or Firm* — Woodard, Emhardt, Moriarty, McNett & Henry LLP

(57) ABSTRACT

A system and method described herein simplifies data entry by a subject of a structured blood glucose test as well as helps with dietary compliance by providing specific dietary suggestions to the user. The system includes a portable device configured to be possessed by the subject. The portable device has a location detection system configured to provide data indicative of the location of the subject. A food database provides to the portable device a list of food items that are limited based on foods available at the location, such as a restaurant. The portable device is configured to receive a selection from the list that is indicative of a food consumed by the subject. A blood glucose meter reads blood glucose readings from the subject. The food database is configured to store the blood glucose readings and information about the foods consumed by the subject. Compliance to a prescribed dietary regimen can be monitored by the user and/or a physician.

46 Claims, 9 Drawing Sheets

(56) References Cited

U.S. PATENT DOCUMENTS

| | | |
|---|---|---|
| 2008/0198012 A1 | 8/2008 | Kamen |
| 2010/0212675 A1 | 8/2010 | Walling et al. |
| 2010/0218132 A1 | 8/2010 | Soni et al. |
| 2010/0312668 A1 | 12/2010 | Notsani |
| 2011/0124996 A1* | 5/2011 | Reinke et al. .................. 600/365 |

OTHER PUBLICATIONS

100 Fabulous iPhone Apps for Your Health and Fitness. Retrieved from the Internet: <URL: http://www.uspharmd.com/blog/2009/100-fabulous-iphone-apps-for-your-health-and-fitness/>.

8 Best Android Apps for Health and Fitness. Retrieved from the Internet: <URL: http://mashable.com/2010/05/01/android-health/>.

Dana Magic Bolus Calculator—Diabetes Health. Retrieved from the Internet: <URL: http://www.diabeteshealth.com/read/2005/07/01/4304/dana-magic-bolus-calculator/>.

Dotti's Weight Loss Zone. Retrieved from the Internet:<URL: http://www.dwlz.com/restaurants.html>.

Good Food Near You. Retrieved from the Internet:< URL: http://www.goodfoodnearyou.com/>.

Top Paid Android Health Apps: Using Android Applications to Track Food Nutrition, Calories and Workout Routines. Retrieved from the Internet: <URL: http://www.brighthub.com/health/technology/articles/93056.aspx>.

* cited by examiner

| Menu Items- For Fast Food Restaurant A- Lunch | | | | | |
|---|---|---|---|---|---|
| | Calories | Carb. | Fat | Protein | Favorite |
| Salad | 90 | 8g | 4g | 4g | ☆ |
| Chili | 185 | 15g | 7g | 12g | ☆ |
| Chicken | 200 | 8g | 11g | 12g | ☆ |

12:14 PM

[Show All Favorites] [Show All] [Show Nearby Restaurants]

*Fig. 5*

LOCATION ENABLED FOOD DATABASE

BACKGROUND

For those with special dietary requirements, such as diabetics, there is a strong need to monitor and control their diet and nutritional needs. As a practical matter, while understanding the need to tightly control their dietary needs, there are a number of obstacles that diabetics experience when trying to control their food intake and accompanying blood glucose levels. If not properly addressed, a number of significant health problems can occur. Thus, there is a need for improvement in this field.

SUMMARY

It has been found that when physicians or other health care providers (HCPs) provide general health recommendations, such as directions to lose weight, exercise more, etc., success in achieving desired results is poor. However, when the physician provides specific dietary and/or exercise goals, the success rate in achieving the goals dramatically improves. For example, if a physician simply says "exercise more" the results are dramatically worse in comparison to prescribing the patient to run five miles a week. Likewise, patients are more likely to follow a dietary regimen that gives precise dietary guidelines, such as ones with specific caloric, carbohydrate, and nutritional goals, than a general recommendation to "eat less."

Even when specific health guidelines are provided, the patient experiences significant obstacles in determining whether they are in fact complying with the recommendation. The patient may become frustrated by the process of wading through and collecting large amounts of data required for monitoring compliance. To put it another way, the more steps it takes, the less likely someone will enter accurate data, if at all. For example, there is a wealth of nutritional information available on the internet, but finding the dietary information that applies to a particular meal can be daunting at best. The patient has to typically wade through vast amounts of information to receive the nutritional information they want. This burden along with being pressed for time decreases the likelihood that they will follow the prescribed program. Moreover, even when the patient finds the correct information, they may learn that the particular meal they intend to eat is not appropriate for the prescribed diet, and as a result, they face the dilemma of ignoring the dietary program by eating the meal anyway or of following the program but dealing with the arduous task of finding alternative meals that meet the dietary goals.

The inventor has developed a unique system and method that simplifies the process for entering meal and other information so as to determine compliance with a prescribed diet. The system automatically filters, sorts, and/or highlights the meal selection options based on the user's location, time of day (e.g., breakfast, lunch, etc.), dietary requirements, and/or historical meal preferences (e.g., favorite meals). This eases entry of the nutritional information because the patient is only presented information pertinent to their location as well as their dietary needs and preferences. For instance, the system has the ability to tailor menu lists based not only on location but also on the time of day as well as rank the alternatives based on dietary requirements and historical selections. By ranking and refining the menu and providing a short list tailored to a particular user, the information can be accurately and easily entered without requiring the user to hunt through multiple alternative selections which can be frustrating. If the available menu items do not meet the particular dietary needs, the system can also suggest nearby establishments, such as other restaurants, that have meals meeting the dietary requirements.

The system is also configured to provide compliance metrics that show how well the user is following the diet based on the foods identified as having been consumed. By doing so, the user can see their compliance trend over time, and if needed, take corrective action to fix any problems. In addition, health care providers can assess how well the user is following the dietary prescription. The physician can also review physiological data, such as blood glucose levels, blood pressure and the like, in order to monitor the health of the patient. If needed, the physician can revise the specific dietary plan for the patient in order to improve results.

In addition, the system integrates the food database with a structured testing regimen. This incorporation of a diet or food database with structured testing is helpful for those tests relying on meal intake, such as an ACCU-CHEK® 360 View assessment and/or insulin to carbohydrate factor optimization. These structured tests rely on accurate knowledge of carbohydrate intake to effectively present reports for treatment optimization purposes. For instance, if the patient or subject of the test is performing an ACCU-CHEK® 360 View assessment and is at home preparing to eat the same breakfast cereal that they do every day, the system would show a favorite for that breakfast meal at the top of the list. After the subject selects this favorite, the information would be provided to the structured test for inclusion into the dataset. This helps to dramatically enhance the structured testing protocol by making easier to enter more accurate dietary information.

Further forms, objects, features, aspects, benefits, advantages, and embodiments of the present invention will become apparent from a detailed description and drawings provided herewith.

BRIEF DESCRIPTION OF THE DRAWINGS

FIG. 5 depicts a menu selection screen for a particular food location.

DESCRIPTION OF THE SELECTED EMBODIMENTS

Figure 1:
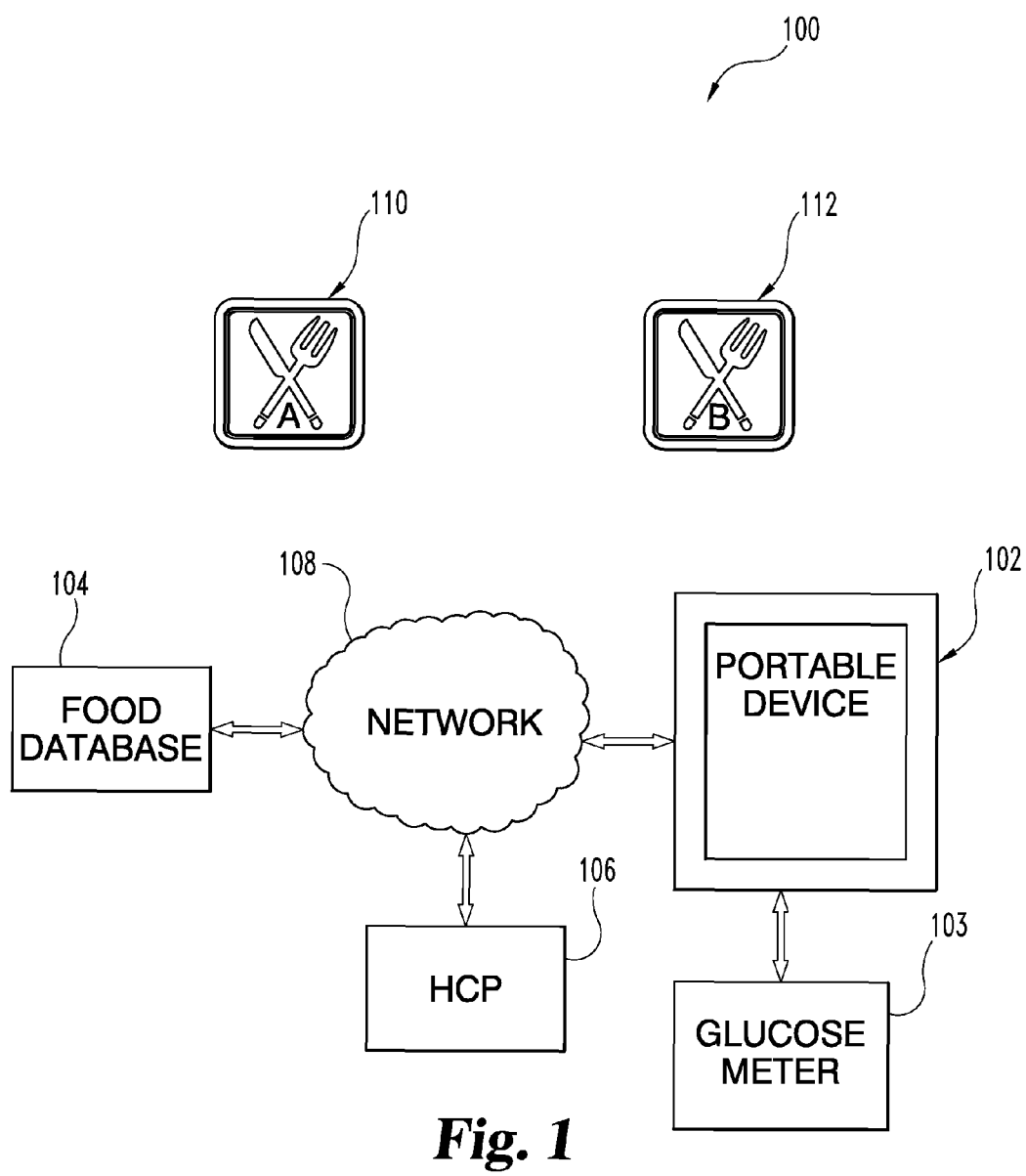
FIG. 1 shows a diagrammatical view of a dietary compliance system according to one embodiment.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

For the convenience of the reader, it should be initially noted that a drawing in which an element is first introduced is typically indicated by the left-most digit(s) in the corresponding reference number. For example, a component identified with a one-hundred series reference number (e.g., 100, 101, 102, 103, etc.) will usually be first discussed with reference to FIG. 1, and a component with a two-hundred series reference number (e.g., 200, 201, 202, 203, etc.) will usually be first discussed with reference to FIG. 2.

The diet compliance system and method described and illustrated herein generally makes it easier for the user to comply with their prescribed dietary regimen. By allowing the physician to select a dietary program specifically tailored for the patient, the chances of the patient following the program are greatly enhanced. Likewise, the user can select a diet, which in turn likely increases the chance for success. Moreover, the system makes data capture for meal and other information simpler such that the user is more likely to enter information, thereby improving compliance tracking for the program. The system also provides automatic feedback to show how well the user is complying to the prescribed dietary regimen. The physician or other health care provider (HCP) as well as the user can readily review the results on an hourly, daily, weekly, monthly, or even yearly basis to determine how well the user is complying with the regimen and, if needed, make adjustments to the diet. By making it simpler for the user to enter food consumption information, more accurate results for structured testing can be easily accomplished.

FIG. 1 shows a block diagram of one example of a diet compliance system 100 that is configured to perform this technique for simplifying data entry for tracking dietary compliance. As can be seen, the diet compliance system 100 includes a portable device 102, a glucose meter 103, a food database 104, and a health care provider (HCP) computer 106. The portable device 102, the food database 104, and the HCP computer 106 communicate with each other via a network 108. The portable device 102 is used by the patient or user to retrieve dietary information from the food database 104 as well as enter information about meal consumption. In one example, the portable device 102 includes a smart phone and/or a cell phone type device such that the portable device is readily accessible to the user. The portable device 102 is used in conjunction with the glucose meter 103 so as to collect glucose readings from the patient. In the illustrated embodiment, the glucose readings are downloaded from the glucose meter 103 onto the portable device 102. The food database 104 contains a database and/or other data structures in which nutritional/dietary information about various foods are stored. For example, the food database 104 can list several hundred restaurants and their caloric, fat, carbohydrate, and fiber information. This information is accessible throughout the system 100 and can be filtered in any number of ways, such as by location. The food database 104 stores information about meal consumption and other patient information collected by the portable device 102. In one example, the food database 104 includes a structured query language (SQL) type database, such as a MICROSOFT® SQL server or ORACLE® type database. Physicians and/or other health care providers use the HCP computer 106 to enter information into the food database 104, such as the patient's prescribed diet and health records, as well as retrieve information to see how well the patient is following the prescribed diet. In one example, the HCP computer 106 includes a personal computer (PC), such as a desktop and/or laptop computer located at the physician's office. To facilitate wide access to the data stored in the food database 104, the network 108 in one example includes a combination of private and public networks, such as a private wireless network that is connected to the internet.

As will be explained in greater detail below, the food database 104 is configured to supply to the portable device 102 a list of potential menu items based on the particular circumstances surrounding the patient. By way of example, the portable device 102 provides customized menu items from which the user can select depending on the location of the patient. In FIG. 1, reference numeral 110 is associated with a first food source location, such as a grocery store or restaurant, and reference numeral 120 signifies a second food source location, such as another grocery store or restaurant, that is different from the first food source location 110. The food database 104 stores a list of food items Returning to the previous example, when the patient is at the first food source location 110, the portable device 120 via the food database 104 filter, sorts (e.g., ranks), and/or highlights the menu items to those available at the first food source location 110 (and not at the second food service location 112). Likewise, when the patient is at the second food source location 112, the portable device 120 filters, sorts, and/or highlights the menu items to those available at the second location 112.

Figure 2:
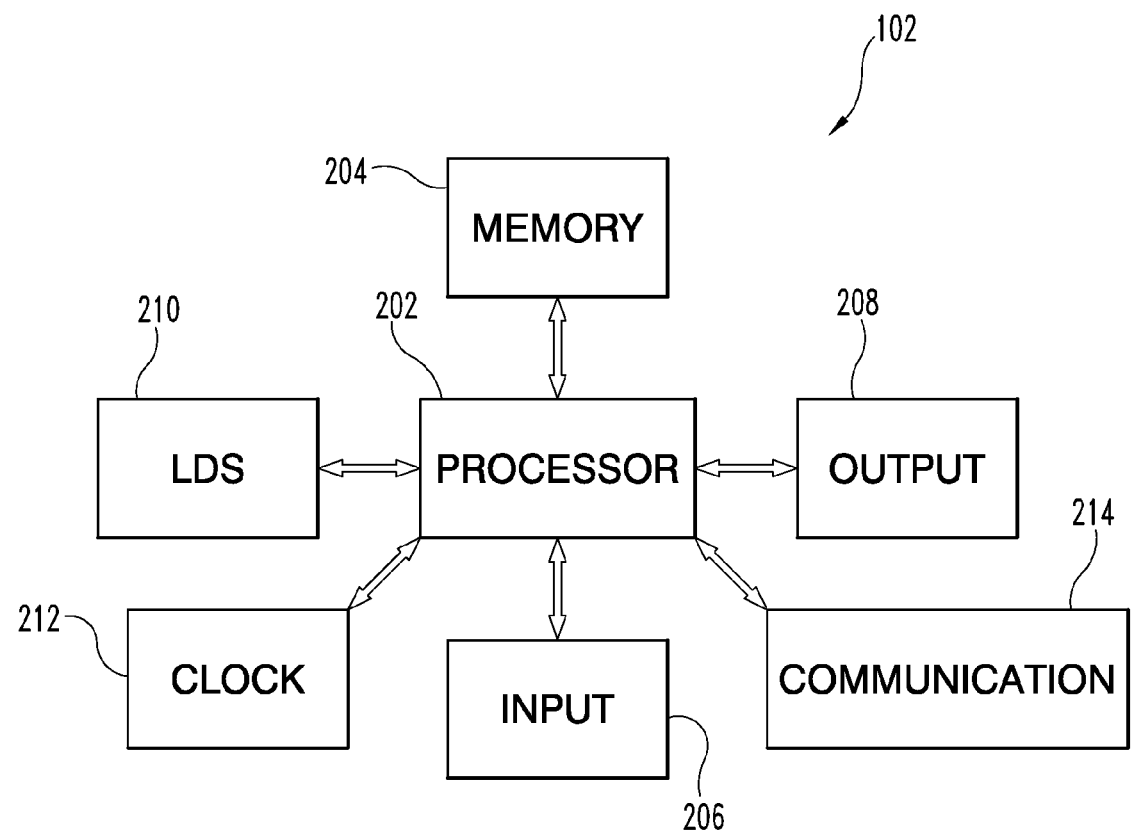
FIG. 2 is a block diagram of a portable device used in the FIG. 1 system.

FIG. 2 shows a block diagram of one example of the components of the portable device 102. As shown, the portable device 102 includes a processor 202 for processing data, memory 204 for storing data, an input device 206 for entering data, and output device 208 for outputting information. The portable device 102 further includes a location detection system (LDS) 210 for detecting the location of the portable device 102, such as a global positioning system (GPS), and/or an assisted GPS-type system. The portable device 102 further includes a clock 212 for determining the time of day for assistance in determining what type of meal (e.g., breakfast, lunch, or dinner) is appropriate at that time. The input device 206 is used to enter data and generally operate the portable device 102, and the output device 208 is configured to provide information to the user. In one example, where the portable device 102 is a smart phone, the input 206 and output devices 208 are combined together into a touch type display. To communicate across the network 108, the portable device 102 includes a communication device 214 that is capable of transmitting information wirelessly and/or via wired-type connections. For example, the communication device 214 can include a transceiver found in cell phones.

Figure 3:
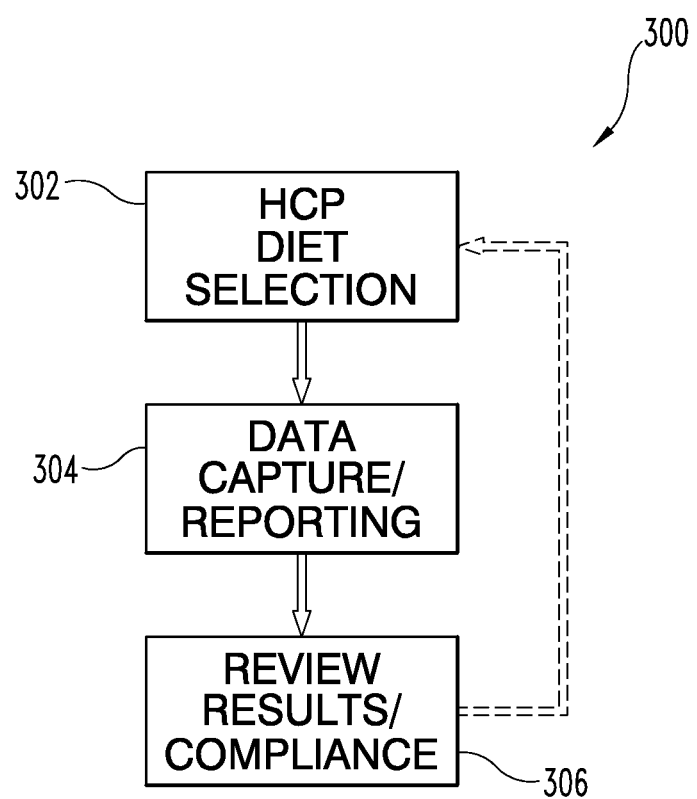
FIG. 3 is a flow chart of an overall technique for specifying a particular diet, capturing data, and reporting compliance.

An overall technique of utilizing the diet compliance system 100 will now be described with reference to a flow chart 300 illustrated in FIG. 3. Looking at flowchart 300, at a data capture stage 302 the health care provider, such as a physician, selects a dietary regimen specifically tailored for the patient. If appropriate, the physician can consult with the patient so as to determine which diet would be best suited for the particular patient's lifestyle. The patient can pick the diet on their own, or if so desired, no diet needs to be selected in certain instances. Referring to FIG. 1, once the physician and/or patient decide upon a dietary regimen, the physician via the HCP computer 106 enters or otherwise associates a particular diet to the patient in the food database 104. The physician can select the diet from a list of predefined diets in the food database 104 or can develop a customized diet specifically tailored to the patient. A particular diet regimen can vary among patients. For example, many diet programs are available such as Atkins, South Beach, Body for Life, as well as those more specific to people with diabetes and those created for the specific user. The system 100 is designed to identify those menu entries, by location, that fit the prescribed or preset diet.

After the diet for the patient is designated, the user is able to utilize the portable device 102 to collect dietary and other data in data capture and reporting stage 304. The user is able to input information, such as meal selection and physiological information, into the portable device 102 via the input device 206. To identify the patient, the portable device 102 can include a unique identifier that is associated with the patient in the food database 104 and/or the patient can utilize a unique user id and password so as to log into the food database 104 via the portable device 102, of example. By identifying the particular patient, the food database 104 via the portable device 102 is able to provide a customized interface so as to, among other things, simplify data entry for the patient. This simplification of the meal entry process also helps to provide more accurate information about the foods that were consumed, which can be quite helpful for structured testing data analysis. By making data entry seamless, the user is more likely to enter information, thereby improving compliance tracking for the diet program. For example, as will be explained in greater detail below, the LDS 210 can help to refine the menu items provided to the user based on their location. The clock 212 can also be used to further refine the available menu items based on the meal that would be appropriate at a particular time of day. In addition, the memory 204 in the portable device 102 and/or the food database 104 can store historical selections to further refine the menu items. In stage 304, the output device 208 of the portable device 102 is able to provide immediate feedback so that the patient is able to monitor how well they are complying with the diet as well as check their health statistics.

To see how well the patient is complying with the prescribed diet as well as monitor the health of the patient, the physician can review the patient results from the food database 104 via the HCP computer 106 in stage 306. For example, the physician can generate a report to see if the patient is exceeding the prescribed daily caloric and/or carbohydrate intake for the diet. If the patient is not properly following the diet, the physician can take correct action to remedy the situation, such as by counseling the patient about the diet. Likewise, if the patient it is not responding to the prescribed diet, the physician can prescribe a different diet and/or a structured test so as to find the source of the problem. Based on how well the patient is complying with the dietary regimen as well as other bodily conditions such as blood glucose levels and blood pressure, the physician can further refine the dietary requirements of the patient, and the process can repeat again as indicated by the dashed arrow in flowchart 300.

Figure 4:
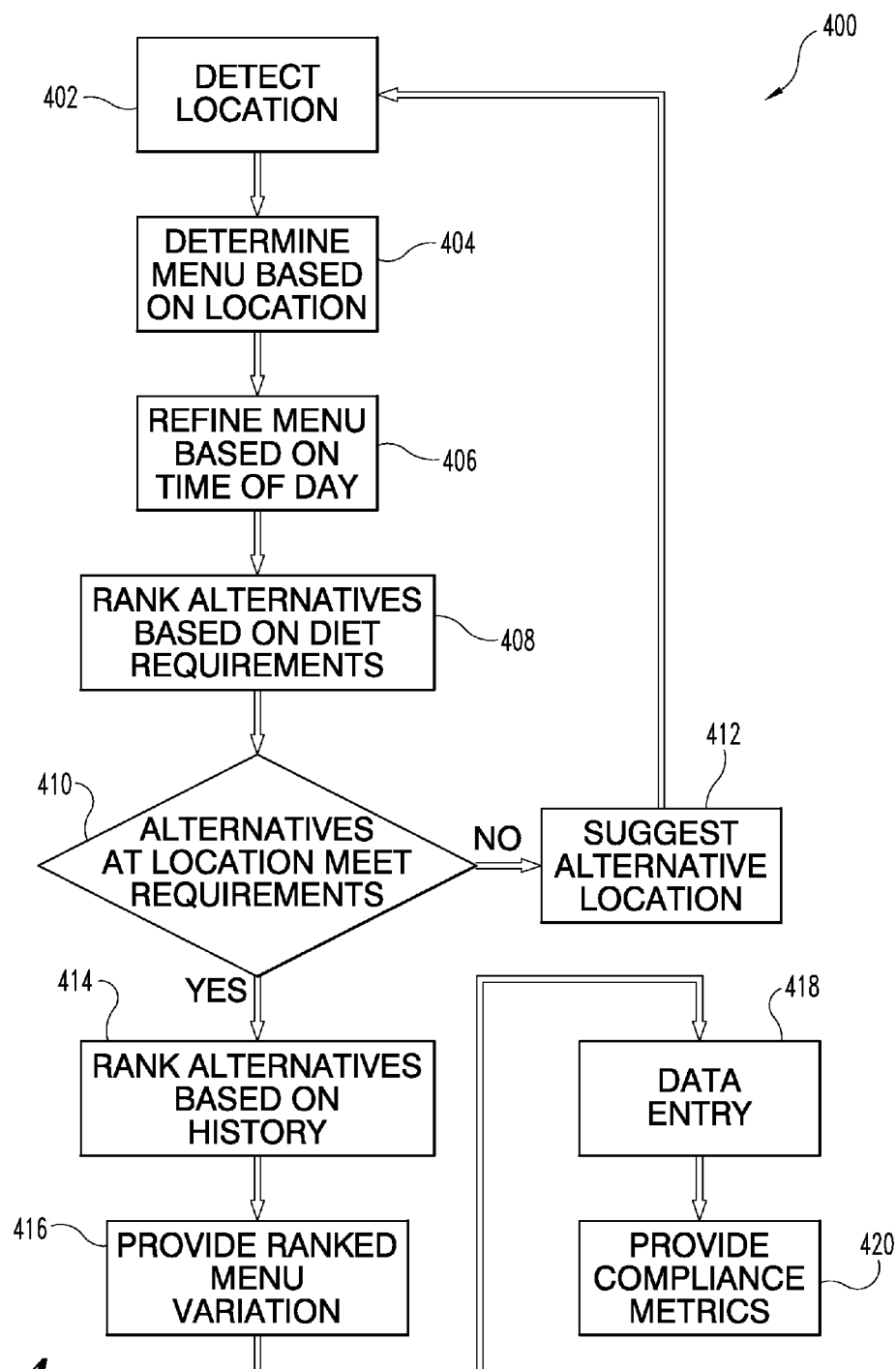
FIG. 4 is a flow diagram that illustrates a technique for selecting food items and providing compliance metrics.

Further expanding upon the ability of the portable device 102 to customize the interface in stage 304, the portable device 102 utilizes a unique technique that allows it to specifically tailor and refine the list of available menu items to reduce the effort required by the user to enter data. Flowchart 400 in FIG. 4 illustrates a technique for simplifying data entry as well as providing compliance metrics. To illustrate this technique, the portable device 102 in this particular example is a smart phone that accesses the food database 104 over the internet. The food database 104 in this example is a web hosted server that provides dietary data to the portable device 102 as well as records patient selected menu items along with other data entered through the portable device 102. With reference to FIGS. 1 and 2, the portable device 102 in stage 402 detects its location with the LDS 210. In this example, the LDS 210 uses GPS coordinates to detect its location. Based on the detected location, the portable device 102 in stage 404 queries the food database 104, and the food database 104 returns a list of menu items for that particular location. For example, if the first food source location 110 in FIG. 1 is a fast food restaurant, the processor 202 via the food database 104 refines the list of available food items based on that location. If the portable device 102 is located at the second food source location 112, then the menu of items would be based on the items available at that location. For example, if the user is following the Body for Life diet (40% carbohydrates, 40% protein, 20% fat), and they show up to a fast food restaurant, the system would prescribe a chicken sandwich and a salad or a bowl of chili as those items that fit the prescribed diet. This ranking of potential food alternatives strongly enables and enforces a diet. Diets tend to state what you cannot have rather than what you can have, which the present system facilitates. In another example, if the user arrives at a restaurant and launches the food database 104, those entries reflecting the restaurant menu entries would be made as "default" (e.g., appearing at the top of the list). Specifically, if the user walks into a McDonald's® restaurant, the portable device 102 would present the menu for the particular McDonald's® restaurant, rather than say a Burger King® restaurant.

Based on the time of day from the clock 212, the processor 202 of the portable device 102 is further able to refine the menu list of available items supplied to the user in stage 406. For example, if it was around lunchtime, then only lunchtime items would be displayed for that particular location rather than items from the breakfast menu. The timing of particular meals can be customized based on the particular circumstances of the user. For instance, shift workers may eat their "breakfast" in the afternoon and their "dinner" in the early morning. In stage 408, the processor 202 of the portable device 102 ranks the food alternatives based on the dietary requirements specified by the physician in stage 302. As an example, if the physician specified a low carbohydrate diet, then items with lower carbohydrates would be ranked higher such that they would appear higher or first on the list as compared to items having higher carbohydrates (or vice-versa). Screenshot 500 in FIG. 5 shows one example of items being ranked based on location. As shown in this particular example, the physician specified a low calorie diet, and the items as shown in screenshot 500 are ranked by calories such that the lower calorie item ("salad") appears at the top of the list, while items having higher caloric values (e.g., "chicken") appear at the end of the list.

Figure 6:
FIG. 6 shows an alert screen when a particular food location does not meet the dietary requirements.

In the event that there is nothing on the menu that meets the prescribed or predetermined diet, the system 100 can use the current location to identify and suggest alternate restaurants in which the diet could be followed. Looking at stage 410 in FIG. 4, the food database 104 determines whether there are any food alternatives at that location that meet the specific dietary requirements. If none exist, the diet compliance system 100 is designed to suggest alternative locations that are close to the user in stage 412. For instance, if the patient is prescribed a purely vegetarian diet, and they are located at a steak house, the food database 104 via the portable device 102 suggests a nearby vegetarian restaurant. Screenshot 600 illustrated in FIG. 6 shows an example of the screen that will display on the output device 208 of the portable device 102 if the restaurant does not meet the dietary requirements. As can be seen, the different food locations are ranked by distance, but in other examples, the list of restaurants or other food locations can be ranked based on other variables, such as those that better meet the dietary requirements of the user. Alternatively or additionally, the ranking of suggested restaurants in stage 412 can also be derived from the preferences of friends, those with similar health issues, those who have the same or similar diets, and/or those with similar profiles provided on one or social media websites, such as on Facebook®, Myspace®, Foursquare®, Yelp®, Urbanspoon®, and the like. For example, restaurants that friends recommended will be ranked or listed higher than restaurants with no or poor reviews. Once an alternative location is selected and the user travels to that location, the portable device 102 again goes to stage 402 to repeat the cycle until the food alternatives meet all of the dietary requirements in stage 410. As one example, if the user approaches an ice cream shop which does not have any items fulfilling the dietary requirements, the portable device 102 could suggest that the user choose a yogurt store that is located within 300 meters as an alternative. In this example the system 100 via the food database 104 has knowledge of the type of food that is being looked at and would suggest an appropriate alternative instead of an inappropriate alternative, such as a steak house or other heavier fare, as an option.

To further help refine the lists to make it easier for the user to make a selection, the portable device 102 via the processor 202 ranks the food alternatives in stage 414 based on previous historical selections. Alternatively or additionally, the food can be ranked based on previous indications of whether or not a particular food item was a favorite for the user. Once the alternatives are ranked in stage 414, the portable device 102 via the output device 208 provides a ranked list of available food items that meet those specific dietary needs in stage 416. Returning to the smart phone example, the list of ranked menu items can appear on the screen of the smart phone in stage 416. Again, screenshot 500 in FIG. 5 shows one example of a list of items ranked for a particular restaurant location, which in this example is Restaurant A. The user has the ability to show only their favorite meals, show all meals, as well as show nearby restaurant or other food locations. The food database can present user created (or system created) favorites stored in the system, but presented in a prioritized list (and/or removed from the list) based on their location and based on the time of day (e.g., meal). The system 100 can automatically create a favorite for a given time of day and location based on repeated meal input. For example, if the user was at home, their favorite meals that they stored at home would be presented by default; however, their favorite meals at McDonald's® would not be presented. If desired, the user can always have access to all of their favorites, but they would not be directly presented—it would require the pressing of a "Show All Favorites" menu selection. Social media can be used for ranking in stage 410. Alternatively or additionally, the ranking of menu items in stage 414 can also be derived from the preferences of friends, those with similar health issues, those who have the same or similar diets, and/or those with similar profiles provided on one or social media websites, such as on Facebook®, Myspace®, Foursquare®, Yelp®, Urbanspoon®, and the like. For instance, menu items that friends like will be ranked higher than menu items with no or poorer ratings. The system 100 also has the ability to track and/or rank dietary information based on the particular restaurant chain visited. As an example, if a person eats at a first McDonalds® restaurant in one state and later visits a second McDonalds® restaurant in a different state, the selections or preferences from the first McDonalds® restaurant are carried over to the second one such that the previous selection affects the ranking of meals in the second McDonalds® restaurant. Moreover, within a particular restaurant chain, store specific menu items can also be tracked and/or ranked.

Figure 7:
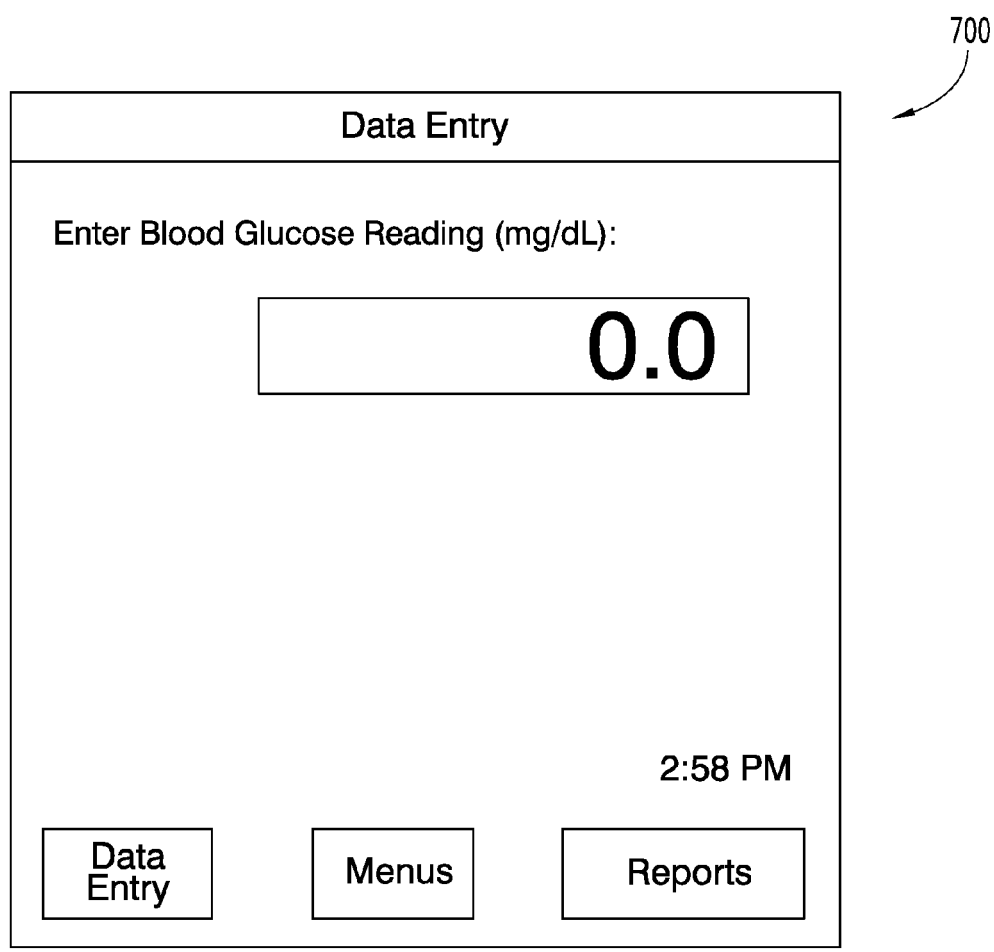
FIG. 7 shows a data entry screen for entering health data.

If needed, the portable device 102 also has the capability of entering data via the input device 206. Referring to FIG. 4, in stage 418 the user is able to enter data such as physiological data and other information related to their health, mental state, environment, and/or other information that is used by the physician for monitoring the patient. For example, in stage 418, the user can enter their blood glucose readings, blood pressure, pulse, and/or other physiological data. Screenshot 700 in FIG. 7 shows just one example of an input screen displayed on the output device 208 in which the user is able to input blood glucose measurements. In another example, a blood glucose meter wirelessly transmits glucose measurements to the smart phone, and in still yet another example, the portable device 102 is a blood glucose meter that automatically records the blood glucose measurements.

Figure 8:
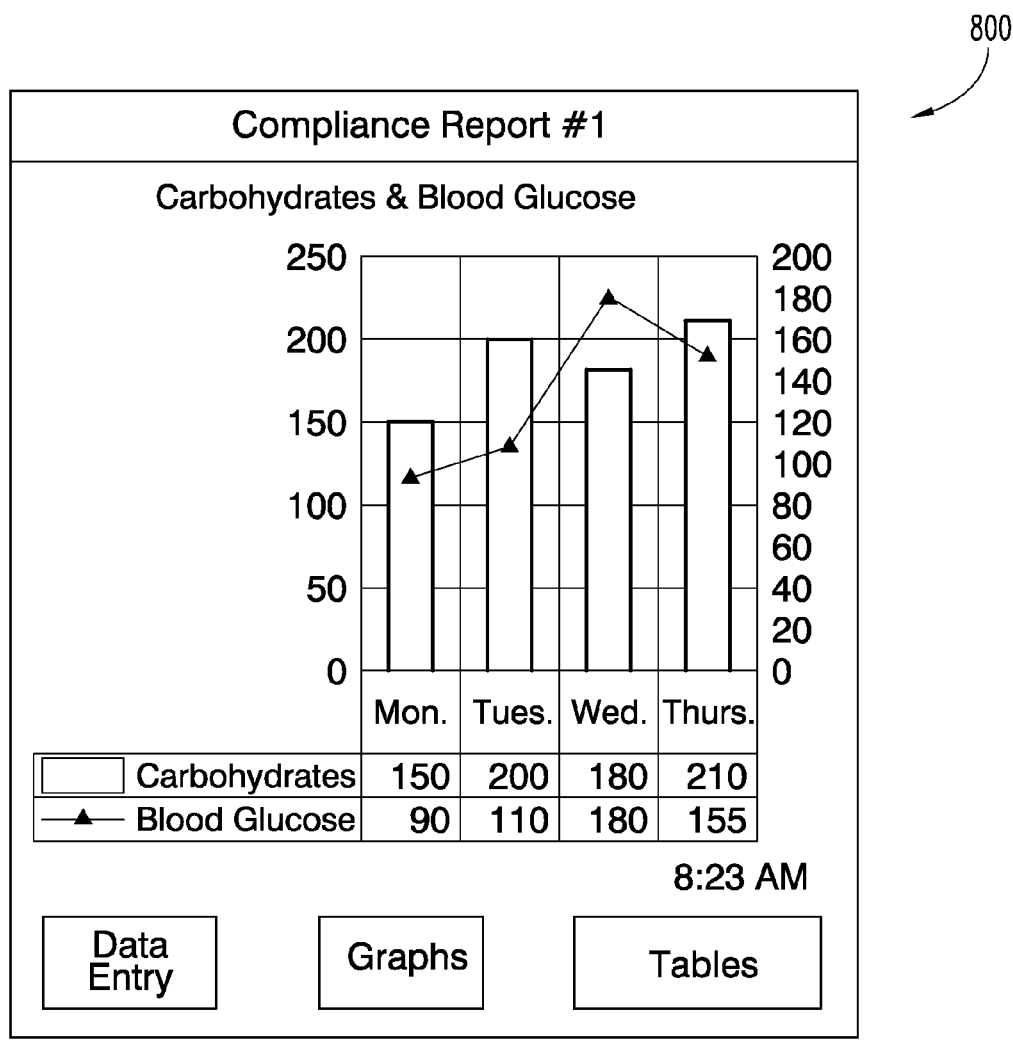
FIG. 8 shows a first compliance report screen.
Figure 9:
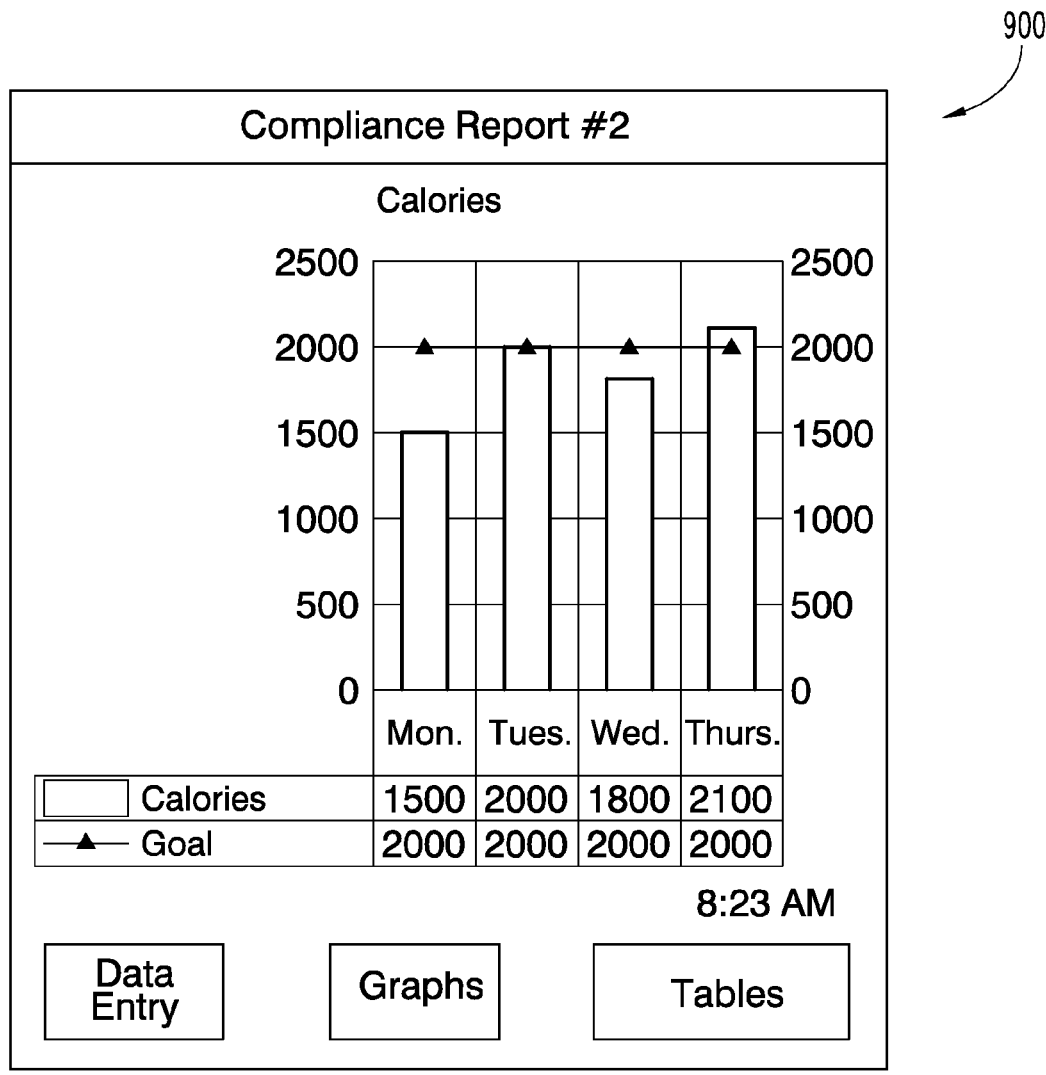
FIG. 9 shows a second compliance report screen.

The portable device 102 is configured to provide feedback so that the user is able to see how they are performing with respect to the prescribed diet as well check their overall health. In stage 420, portable device 102 and/or the HCP computer 106 are able to provide compliance metrics on how well the individual is complying with their dietary regimen. FIG. 8 shows a screenshot 800 for one example of a compliance report that can be displayed on the output device 208 of the portable device 102. FIG. 9 shows another display screen 900 that is used to show how well the individual is complying with their specific dietary requirements. By making it easier for the user to instantaneously check on their compliance for a particular dietary regimen, the user is provided with better feedback to ensure they are properly complying with their dietary and nutritional regimen.

In one particular use example, the physician via the HCP computer 106 inputs a specific low carbohydrate diet for the patient into the food database 104. As mentioned before, the food database 104 includes a wealth of information about the particular diet as well as information about which food items that would be appropriate or inappropriate for the prescribed low carbohydrate diet. The user carries a portable device 102 in the form of a smart phone that includes a GPS subsystem that is able to detect the location of the user. Most information storage and processing is performed on a remotely hosted food database 104 that the smart phone accesses over the internet. The smart phone accesses the food database 104 using either a proprietary client program or through a standard web browser, such as one using the HTML5 standard or other variations. In this remotely hosted configuration, the smart phone is not constrained by memory and/or processing power limitations. The smart phone continuously or periodically transmits its GPS coordinates to the food database 104. Based on the location from the GPS, the food database is able to prioritize nutritional information about food served at various nearby locations such as restaurants, hotels, supermarkets, and/or even at home. This information is transmitted from the food database 104 and displayed on the smart phone as a web page. For instance, if the user arrives at a restaurant such as a fast food restaurant and launches an application on their cell phone which contains the dietary information, the entries reflecting the menu for the particular location would appear by default.

To help further refine the choices and reduce the results to make the selection process easier for the user, the food database 104 further refines the menu list based on the time of day, such as whether it is breakfast, lunch, or dinner, as well as on historical meal selections. In this low carbohydrate use example, the user enters the restaurant during breakfast. The food database 104 would display on the smart phone a list of menu items with the low carbohydrate breakfast items, such as eggs, being displayed at the top of the list, while higher carbohydrate items, such as pancakes and toast, are displayed near the bottom of the list. Other nutritional information, such as fat, caloric, and carbohydrate content, are displayed along side a description of the item. Social media reviews of the menu items and/or the restaurant can also be displayed. The food database 104 even suggests on the smart phone a particular breakfast item that was suggested by a friend with a similar diet from information gleaned from social media network data. By providing specific menu items based on the dietary needs, the user is able to better comply with their diet program. In the event that there are no items available that meet the user's dietary requirements, for example the user visits a pancake buffet, the smart phone can suggest alternative nearby restaurants with lower carbohydrate meal options. By having a refined menu selection, the user is able to quickly and effortlessly input particular information about their meals. The accuracy of the entered information is also improved.

Compliance metrics showing how well the user is complying with their daily dietary requirements can be instantly provided on the smart phone so that the user can take corrective action. The user for example may notice that they are close to their daily carbohydrate limit, and therefore, they may decide to eat a lighter, high protein meal instead of a pasta dinner. The physician in this example also requires that the patient measure and record their blood glucose levels before and two hours after each meal as a part of a structured test. Following the physician's orders, the patient measures their blood glucose with a blood glucose meter that wirelessly transmits the glucose readings to the smart phone which in turn automatically transmits the data to the food database. The physician is then able to instantaneously monitor the health of the patient and take corrective action, if needed. For instance, the food database can alert the physician of a hypoglycemic or near hypoglycemic event. The physician can review a web page showing specific information about the prior meals in conjunction with other collected data, such as glucose, activity, and energy levels, on the HCP computer 106 so as to locate a potential source for the hypoglycemia. When appropriate, the physician can even remotely modify or change the prescribed diet without even requiring the patient to visit the office.

As alluded to above, the above described technique and system can be especially helpful for structured testing programs, such as with an ACCU-CHEK® 360 View Blood Glucose Analysis system, because data entry is simplified and data accuracy is improved. One non-limiting example of structured testing protocols that can be used is described in U.S. patent application Ser. No. 12/710,430, which is hereby incorporated by reference, but other structured testing protocols can be used as well. The simpler it is to enter meal and other information, the more likely the subject of the test will properly perform the structured test. Structured, self-monitoring blood glucose (SMBG) testing regimens are typically conducted so as to locate possible sources for diabetic control problems and determine the proper therapeutic response, whether it be changes to diet, exercise, and/or medication. In structured testing, the physician prescribes a predefined testing regimen in which blood glucose readings are collected in conjunction with one or more other variables so as to determine a possible source for a glucose control problem. While blood glucose levels, exercise, and medication dosages can easily be quantified and tracked by the patient or subject, quantifying information about the meals consumed can be quite difficult. For instance, a diabetic subject can quite easily quantify and accurately record their blood glucose levels, how many miles they ran (and for how long), and how much insulin they injected, but when it comes to quantifying the calories, carbohydrates, fats, and other nutritional information about the meals they consumed, it can be an extremely difficult proposition. At best, most structured tests ask the diabetic to identify whether the meal size was small, medium or large, which provides little useful information. Moreover, individuals in general tend to underestimate the size and/or caloric content of meals. With the technique and system described above, the subject is in a better position to quantify the meals consumed for structured testing, which in turn provides better data upon which the physician is able to diagnose and address a particular issue. The physician is able to analyze dietary numerous factors, such a calories, carbohydrates, etc., that may be a source for hypoglycemia or hyperglycemia in the diabetic subject.

It should be appreciated that the system and techniques described above can be adapted in other ways for numerous other types of use case scenarios and/or environments. To illustrate some other use case scenarios, a few more examples will now be provided. In one use case example, the user wants to run a testing in pairs structured test. In this type of structured test, the user takes a blood glucose reading, does something, and then takes another blood glucose sample at some time in the future. This testing in pairs technique shows any coupling or relationship between the two blood glucose readings and the action/event. To illustrate this more specifically, consider a case in which the user wants to see the impact of consuming their favorite milkshake. The user initiates the testing in pairs structured test, and the portable device 102 prompts the user to take a blood glucose reading. Using the food database 104, the user selects the milkshake once it is consumed. Two hours later, the portable device 102 awakens and prompts the user to take a second blood glucose reading. The single food input (i.e., the milkshake entry) is not only associated with one blood glucose reading in the database, but is also associated with the two blood glucose readings. It is envisioned that that more than two blood glucose readings can be associated with an individual food entry in the food database 104 (and vice versa). For instance, a single food input in one example can be associated with up to six blood glucose samples.

In another use case scenario, a structured test is performed to determine the insulin to carbohydrate ratio of the user during the morning or breakfast part of the day. On the given morning of the test, the portable device 102 prompts the user to take a blood glucose reading and then eat a meal of a predetermined size. Via the food database 104 and the portable device 102, the user identifies a typical morning breakfast they eat at home and subsequently consumes the breakfast. For every hour after eating breakfast, the portable device 102 collects blood glucose readings, and this continues until six measurements are taken. Afterwards, the portable device 102 and/or the food database 104 compares the blood glucose reading at the start of the test with the blood glucose reading at the end of the test, and utilizes this difference as well as the meal size and speed from the food database 104 to calculate the insulin to carbohydrate ratio for the specific meal consumed. In this example, the collected data is used to calculate the results of a structured test without the need to select a specific diet.

As another example, the user and the physician do not select any particular diet to follow, but instead, the physician wishes to use the system to simply perform a structured test. When the portable device 102 asks the user to enter meal information for the test, the user can enter the meal using the food database 104. Alternatively, the user can manually input information about the meal (e.g., carbohydrates, size, calories, etc.) without using the food database 104. Subsequently, the data from the structured test is analyzed by the physician.

For still yet another example of a use case scenario, the user decides that they want to follow the South Beach Diet® and programs the system accordingly. The system 100 supports the user in following the diet in manners as described above, such as by providing menu items suitable for the South Beach Diet® and diet compliance metrics. Upon visiting the physician, both the user and physician decide on a different dietary program, and the physician enters the new diet via the HCP computer 106. As a result, the system 100 will no longer support the previously selected South Beach Diet® for the user; instead, the system 100 provides support for the newly selected diet.

As should be recognized, these techniques and system can be adapted to collect additional information and/or provide additional functionality. For instance, the food consumption information that is facilitated by the food database 104 can be used by a bolus calculator. As a result, the bolus calculations can be tailored to the particular individual. For structured testing purposes as well as for other purposes, the system 100 can be used to collect other information, such as exercise information, stressors, and the like, and align or associate the information with particular meals. Alternatively or additionally, the location coordinates of the user can be directly associated with individual glucose readings so as to determine, among other things, if location might be indicative of a glucose issue. Within the food database 104, meal rises in blood glucose readings (e.g., the change in blood glucose levels between pre-meal and 2 hours after the meal) can also be associated with particular meals consumed. In another example, the pre- and post-meal blood glucose readings are stored in meal groupings within the food database. Meal groupings can be created based on common traits shared between meals. For example, meals eaten at particular times and/or that share common foods can be used to form meal groupings. It should be appreciated that other characteristics can be used to form or identify meal groupings. The data from these meal groupings can be statistically processed (e.g., mean, median, minimum, maximum, mode, range, etc.) and stored such that the impacts from various meal groupings can be used to identify problems. The system 100 can also be configured to track existing therapies for the user so that if the therapy changes, the system 100 can accordingly help in developing a recommended dietary change.

The illustrated and above-described system and techniques are just but a few examples, and it is contemplated that numerous other examples are possible. For example, the system 100 in FIG. 1 can be configured differently on other embodiments. For instance, the portable device 102 was described as being a smart phone and/or a cell phone type device, but in other examples the portable device 102 can take other forms including, but not limited to, portable computers, such as tablets, laptops, portable digital assistants, and/or health monitoring systems, such as blood glucose meters, blood pressure monitoring devices, and/or portable cardiac monitoring devices, to name just a few examples. The food database 104 was described as being a structured query language (SQL) type database, such as a MICROSOFT® SQL server or ORACLE® type database residing on web hosted server type computer, but it is envisioned that other types of data storage and processing systems can be used. For instance, the food database 104 can wholly or partially reside on portable device 102, the HCP computer 106, and/or across a distributed network, just to name a few alternatives. When the food database 104 is web enabled, a wide array of locations can be supported, and the portable device 102 would not be constrained by memory size and processing power limitations. The HCP computer 106 in one example includes a personal computer (PC), such as a desktop and/or laptop computer. However, in other examples, the HCP computer 106 can include tablet-type computers, smart phones, cell phones, terminals, as well as other components that allow electronic data entry and/or manipulation.

The various components of the system 100 communicate internally and/or across the network 108 by sending and receiving various signals. While the network 108 was described as including the internet, the network 108 can include any form of a communication network, such as telecommunication systems, cellular communication systems, the internet, one or more other wide area networks (WAN), a local area network (LAN), a proprietary network, an institutional network, a cable television network, a public switched telephone network (PSTN), a combination of these, and/or other types of networks generally known to those skilled in the art. Components of the system 100 can be communicated across the network 108 in any number of manners, such as in a continuous, periodic, synchronous and/or asynchronous manner. It is contemplated that the network 108 may not be needed in other examples. For instance, when the food database 104 resides on the portable device 102, the portable device 102 can be programmed directly by the physician and/or through a direct connection with the HCP computer 106, such as via a USB port.

The first and second food source locations 110, 112 include any location where food may be provided. By way of non-limiting examples, the first and second food source locations 110, 112 can include restaurants, pubs, hotels, supermarkets, residential homes, clubs, and/or fast food restaurants, to name just a few examples. In the example shown in FIG. 1, two food source locations are illustrated, but it should be envisioned that the database can store information for many more food source locations.

In the illustrated embodiment, the portable device 102, glucose meter 103, food database 104, HCP computer 106, and network 108 are illustrated as separate components. One or more of these components can be combined together into a single unit. For example, instead of the food database 104 being separate from the portable device 102, the information of the food database 104 can be incorporated into the portable device 102. As another example, the HCP computer 106 can be incorporated with the food database 104 to form a single unit. While the glucose meter 103 is depicted as communicating to the other components through the portable device 102, the glucose meter 103 in other examples can directly communicate or transfer information to the other components via the network 108. Furthermore, selected components may not necessarily need to communicate via the network 108. For example, the HCP computer 106 can communicate directly with the food database 104 without the need of a network and vice versa. While the portable device 102 is illustrated as a unitary system, it also should be appreciated that the portable device 102 can include multiple components that communicate with one another. For example, the portable device 102 can include a cell phone such as a smart phone that communicates via Bluetooth™ with the blood glucose meter 103. Likewise, the HCP computer 106 and the food database 104 can be configured from multiple components that are integrated together.

The portable device 102 can be configured differently than what is shown in FIG. 2. As noted before, the processor 202 is used to control the operation of the portable device 102. As should be recognized, the processor 202 in conjunction with the other components of the portable device 102 can partially or fully perform the acts in the methods described, illustrated, and/or claimed herein. For example, the processor 202 can be programmed to provide to the subject (e.g., via the output device 208) a list of food items in which the foods available at the particular location are at least emphasized. It also should be appreciated that the processors in other devices of the system, such as in the glucose meter 103, the food database 104, and/or the health care provider computer 106, can partially or fully perform the acts in the methods described, illustrated, and/or claimed herein. The processor 202 may be comprised of one or more components. For a multi component form of processor 202, one or more components may be located remotely relative to the others, or configured as a single unit. Furthermore, processor 202 can be embodied in a form having more than one processing unit, such as a multi-processor configuration, and should be understood to collectively refer to such configurations as well as a single-processor-based arrangement. One or more components of the processor 202 may be of electronic variety defining digital circuitry, analog circuitry, or both. Processor 202 can be of a programmable variety responsive to software instructions, a hardwired state machine, or a combination of these. The clock 212 is used to time events in the portable device 102. As should be appreciated, the clock 212 can be incorporated into the processor 202 or can be a stand-alone component. Further, the clock 212 can be hardware and/or software based.

Among its many functions, the memory 204 in conjunction with the processor 202 is used to store nutritional and dietary information along with the user entered meal selection and health information on a temporary, permanent, or semi-permanent basis. Memory 204 can include one or more types of solid state memory, magnetic memory, or optical memory, just to name a few. By way of nonlimiting example, the memory 204 can include solid state electronic random access memory (RAM), sequential access memory (SAM), such as first-in, first-out (FIFO) variety or last-in, first-out (LIFO) variety, programmable read only memory (PROM), electronically programmable read only memory (EPROM), or electronically erasable programmable read only memory (EEPROM); an optical disc memory (such as a blue-ray, DVD or CD-ROM); a magnetically encoded hard disc, floppy disc, tape, or cartridge media; or a combination of these memory types. In addition, the memory 204 may be volatile, non-volatile, or a hybrid combination of volatile, non-volatile varieties. The memory 204 can further include removable types of memory. The removable memory can be in the form of a non-volatile electronic memory unit, optical memory disk (such as a blue ray, DVD or CD ROM); a magnetically encoded hard disk, floppy disk, tape, or cartridge media; a USB memory drive; or a combination of these or other removable memory types.

With continued reference to FIG. 2, the input device 206 can include any type of input device as would occur to those skilled in the art, such as buttons, microphones, touch screens, keyboards, and the like, to name a few examples. The output device 208 can include output devices of the type as would occur to those skilled in the art, such as displays, tactile devices, printers, speakers, and the like, to name a few examples. Moreover, it should be recognized that the input device 206 and the output device 208 can be combined to form a single unit such as, for example, a touch-type screen. While the output device 208 of the portable device 102 was described as providing the refined and/or ranked list of food items, it should be appreciated that other output devices that are separate from the portable device 102 can provide the list. For instance, the portable device 102 can be used to locate the user, but a separate electronic menu at the restaurant displays the list of food items specifically tailored to the subject. The LDS 210 can include any type of system for location detection that can be hardware and/or software based. For example, the LDS 210 can include a global positioning system (GPS), an assisted GPS-type system, a compass, and/or an accelerometer, as well as other components for detecting the position or location of the portable device 102. In another example, the food database 104 can directly locate the portable device 102 without receiving location coordinates from the portable device 102. In this example, the food database 104 triangulates the location of the portable device 102 based on the internet protocol (IP) addresses of one or more routers with known locations through which the portable device 102 communicates. In another example, the location of the portable device can be determined based on the location of a Wi-Fi hotspot through which the portable device 102 communicates, Combinations of techniques can be also used for location detection. For instance, the portable device 102 can be located based on some combination of Wi-Fi router location data, 3G/4G cellular tower location data, and GPS coordinate data. The system 100 also allows the user to manually enter their location, such as when GPS line of sight is not available. The communication device 214 can include any type of device and/or software that is able to communicate across the network 108. For instance, the communication device 214 can include a cellular communication type device, a Wi-Fi type device, and/or an infrared port, to name just a few.

In the techniques described above, physician and/or patients were described as performing certain acts, but it should be appreciated that others can partially or entirely perform the acts. For example, a physician assistant, nurse, administrator, dietician, and/or third party may perform the acts described with reference to the physician, and a family member, nurse, assistant, employees, or other individuals may help the patient to enter information into the portable device 102 or elsewhere. It should be appreciated that others may enter and/or prescribe the dietary regimen. In one particular example, the physician may mail or send via facsimile a form to a centralized location in which the dietary regimen is entered into the food database 104. The physician and/or the patient can also enter the dietary regimen via the portable device 102. As mentioned before, the patient can also select the dietary regimen. As a case in point, imagine the patient would like to follow the South Beach Diet® or the like. Based on the location of the patient, the system 100 highlights foods at the location that comply with the diet. Later on in this example, if the physician prescribes a different diet, the system 100 would then override the prior patient-selected diet in favor of the new diet plan prescribed by the physician. While the physician, other health care providers (e.g., a dietician), the patient and/or others can help select a dietary approach in stage 302 (FIG. 3), it is contemplated that this system 100 and technique can be used in situations where no dietary approach is selected or prescribed. In the event that no diet is selected in stage 302, the user is still able to enter information, such as meals consumed and blood glucose readings. However, given that no diet is designated, the system 100 would not be able to support reporting of dietary compliance metrics, but the system 100 would still be able to support other functions. In other words, the system 100 is still able to capture data and provide the data for structured testing purposes even when no dietary approach is selected.

With respect to providing information, such as food, meals, dietary compliance, and restaurant information, it should be recognized that the system 100 at least emphasizes relevant information so as to simplify the selection process by the user. As used herein, the term "emphasize", or any variation of this term (e.g., "emphasized"), means any manner in which the relevant information is pointed out and/or called to the attention of the user so that the user is able to readily identify the relevant information. By way of nonlimiting examples, the provided information can be emphasized by reducing the amount of information provided (e.g., limit items on the list), ranking the information, filtering the information, sorting the information, highlighting the information, bolding the information, underlining the information, increasing the volume when the information is played, and/or color coding the information, to name just a few.

In one example, the list of available restaurants or other food locations is limited based on the location of the user, and then the foods or meals are ranked based on how well they comply to the user's diet. However, there are other possibilities which help simplify the selection process. Using an example of a hierarchical approach, the restaurant names first appear based on location. Upon selecting a restaurant, a ranked order of menu items or foods are then displayed with previously selected items being highlighted. It should also be appreciated that the interface can differ from what is shown in the drawings. For the visually impaired as well as for others, the portable device 102 in one example uses text to speech (and speech to text) technology to interface with the user, and in other variations, a display is used to interact with the user. As another example, the listing of food items can incorporate two tabs, one listing meals and the other listing individual food items. To customize and/or generate information about a particular meal, the user can combine one or more food items under the food items tab to create a meal. Moreover, the user can manually enter meal information not appearing in the food database 104.

The various stages for the techniques described above can be performed in an order different than that described above and/or illustrated in the drawings. For example in FIG. 4, the menu of food items can be refined based on time (stage 406) after the menu items are ranked on historical selections (stage 414). During the data capture and reporting stage 304, the information contained in all or part of the food database 104 may reside on the portable device 102. For example, where network coverage for smart phones is not readily available, the entire food database 104 may reside in the memory 204 of the portable device 102. In contrast, where network communication is readily available, only the required information from the food database 104 is transmitted via the network and temporarily stored in the memory 204 of the portable device 102.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The Invention claimed is:

1. A method for obtaining information about foods consumed by a subject of a blood glucose test, the method comprising:
    determining a location of a portable device possessed by the subject;
    providing to the subject a list of food items in which foods available at the location are at least emphasized, wherein said providing to the subject the list of food items includes emphasizing the foods available at the location by sorting the list of food items based on proximity to the subject;
    receiving a selection from the list that is indicative of a food consumed by the subject; and
    collecting a blood glucose reading from the subject.

2. The method according to claim 1, wherein said providing to the subject the list of food items further includes at least emphasizing the food items in the list based on historical food preferences of the subject.

3. The method according to claim 1, wherein said providing to the subject the list of food items further includes at least emphasizing the food items in the list based on dietary requirements of the subject.

4. The method according to claim 1, wherein said providing to the subject the list of food items further includes at least emphasizing the food items in the list based on time of day.

5. The method according to claim 1, further comprising ranking the food items on the list based on dietary requirements of the subject.

6. The method according to claim 1, further comprising providing via the portable device metrics showing compliance of the subject to a diet.

7. The method according to claim 1, further comprising:
    determining the location lacks food items that meet dietary requirements for the subject; and
    providing via the portable device a list of alternative locations that meet the dietary requirements for the subject.

8. The method according to claim 1, wherein all of the recited acts are performed by the portable device.

9. The method according to claim 1, wherein the recited acts are all or in part performed by a food database that is located remotely from portable device.

10. The method according to claim 1, wherein said collecting the blood glucose reading includes receiving the blood glucose reading from a blood glucose meter.

11. The method according to claim 10, wherein the blood glucose meter is integrated into the portable device.

12. The method according to claim 1, wherein said providing to the subject the list of food items includes displaying the list of food items on the portable device.

13. The method according to claim 1, further comprising associating the food consumed by the subject to the blood glucose reading in a food database.

14. The method according to claim 1, wherein the consumed food and the blood glucose reading are stored together with a time stamp.

15. The method according to claim 1, further comprising associating the food consumed to the blood glucose reading when the food consumed and the blood glucose reading occur within a defined time interval.

16. The method according to claim 1, further comprising triggering a reminder system after a defined period of time after said receiving the selection.

17. The method to claim 1, further comprising providing results of the blood glucose test to a health care provider computer.

18. The method to claim 1, wherein said providing to the subject the list of food items includes emphasizing the foods available at the location by filtering the list of food items to provide only those available at the location.

19. The method according to claim 1, further comprising:
    storing the blood glucose reading and the selection of the food consumed in memory; and processing at least the blood glucose reading and the selection of the food consumed to indentify any patterns for a structured blood glucose test.

20. The method to claim 1, wherein said receiving the selection and said collecting the blood glucose reading occur at different times.

21. The method according to claim 1, further comprising:
collecting insulin dosing information from the subject with the portable device.

22. The method according to claim 1, further comprising:
collecting meal information from the subject with the portable device.

23. The method according to claim 1, further comprising:
collecting blood glucose measurements from the subject with the portable device.

24. The method according to claim 23, further comprising:
collecting insulin dosing information and meal information from the subject with the portable device.

25. A method, comprising:
receiving with a food database a diet regimen;
receiving with the food database location data corresponding to a location of a portable device that is with a subject;
determining the location lacks food items that meet dietary requirements for the subject;
generating with the food database a list of alternative locations that meet the dietary requirements for the subject;
ranking the list of the alternative locations based on distance from the location of the portable device; and
outputting the list of the alternative locations to the subject after said ranking.

26. The method according to claim 25, further comprising receiving with the food database blood glucose readings from the subject.

27. The method according to claim 25, wherein the diet regimen is prescribed by a physician.

28. The method according to claim 25, wherein the diet regimen is selected by the subject.

29. The method according to claim 25, wherein the portable device is a cell phone.

30. The method according to claim 25, further comprising receiving information about a meal consumed by the subject that was created by the subject selecting more than one item from the list.

31. The method according to claim 25, wherein the location is a restaurant.

32. The method according to claim 25, wherein the location is a residence.

33. The method according to claim 25, wherein the location is a grocery store.

34. A system for obtaining information about foods consumed by a subject of a structured blood glucose test, comprising:
a portable device configured to be possessed by the subject, the portable device having a location detection system configured to provide data indicative of the location of the portable device;
a food database configured to provide to the portable device a list of food items at least emphasizing foods available at the location by sorting the list of food items based on proximity to the subject;
wherein the portable device includes
an output device configured to display the list of food items and
an input device configured to receive a selection from the list that is indicative of a food consumed by the subject;
a blood glucose meter configured to read blood glucose readings from the subject; and
wherein the food database is configured to store the blood glucose readings and information about the foods consumed by the subject.

35. The system according to claim 34, wherein the food database is separate from the portable device.

36. The system according to claim 34, wherein the food database is incorporated into the portable device.

37. A system for obtaining foods consumed by a subject of a blood glucose test, comprising:
a portable device configured to be possessed by the subject;
a location detection system configured to determine the location of the portable device; and
the portable device including
a processor configured to process a blood glucose reading from the subject wherein the processor is configured to determine the location lacks food items that meet dietary requirements for the subject, wherein the processor is configured to generate a list of alternative locations that meet the dietary requirements for the subject,
an output device configured to provide the list of the alternative locations ranked based on distance from the location of the portable device, and
an input device configured to receive a selection from the list indicative of a food consumed by the subject.

38. The system according to claim 37, further comprising memory to store the selection from the list indicative of the food consumed by the subject.

39. The system according to claim 38, wherein the memory is configured to store the selection together with the blood glucose reading.

40. The system according to claim 37, further comprising a food database configured to supply to the processor the list of food items.

41. The system according to claim 40, wherein the food database is separate from the portable device.

42. The system according to claim 37, wherein the location detection system is incorporated into the portable device.

43. The system according to claim 37, wherein the location detection system is separate from the portable device.

44. The system according to claim 37, further comprising a blood glucose meter configured to measure the blood glucose reading from the subject.

45. The system according to claim 44, wherein the blood glucose meter is incorporated into the portable device.

46. The system according to claim 44, wherein the blood glucose meter is separate from the portable device.

* * * * *